US009867388B2

(12) United States Patent
Tomkins

(10) Patent No.: US 9,867,388 B2
(45) Date of Patent: Jan. 16, 2018

(54) PARTIAL CALCIFICATION OF FREE FATTY ACID MIXTURES, LIVESTOCK FEED COMPOSITIONS INCLUDING THEM, AND METHODS OF MAKING SAME

(71) Applicant: Milk Specialties Global, Eden Prairie, MN (US)

(72) Inventor: Trevor Tomkins, Sycamore, IL (US)

(73) Assignee: MILK SPECIALTIES COMPANY, Carpentersville, IL (US)

( * ) Notice: Subject to any disclaimer, the term of this patent is extended or adjusted under 35 U.S.C. 154(b) by 118 days.

(21) Appl. No.: 14/814,936

(22) Filed: Jul. 31, 2015

(65) Prior Publication Data
US 2016/0007631 A1 Jan. 14, 2016

Related U.S. Application Data

(62) Division of application No. 12/755,800, filed on Apr. 7, 2010, now Pat. No. 9,126,921.
(Continued)

(51) Int. Cl.
A23D 7/00 (2006.01)
C07C 51/00 (2006.01)
A23K 20/158 (2016.01)
C07C 51/41 (2006.01)
C11C 3/00 (2006.01)
C11C 1/02 (2006.01)
(Continued)

(52) U.S. Cl.
CPC ............ *A23K 20/158* (2016.05); *A23K 20/24* (2016.05); *A23K 20/30* (2016.05); *A23K 40/10* (2016.05);
(Continued)

(58) Field of Classification Search
CPC ........ C07C 51/41; C07C 51/00; C07C 51/412; C11C 3/00; C11C 1/025; A23K 20/158;
(Continued)

(56) References Cited

U.S. PATENT DOCUMENTS 4,016,296 A 4/1977 DeSantis
4,062,988 A 12/1977 DeSantis
(Continued)

FOREIGN PATENT DOCUMENTS

ES 2143936 B1 * 5/2000

OTHER PUBLICATIONS

ES2143936A1 English Abstract, May 2000.*
(Continued)

*Primary Examiner* — Emily Le
*Assistant Examiner* — Subbalakshmi Prakash
(74) *Attorney, Agent, or Firm* — Mueting, Raasch & Gebhardt, P.A.

(57) ABSTRACT

The present invention includes a nutritional supplement composition that may be used for livestock and the like, as well as to a livestock feed mixture containing same. Also included are methods of preparing the nutritional supplement composition, the livestock feed mixture, as well as methods of providing nutrition to livestock and the like. The livestock feed composition comprises: (a) a solid particulate livestock feed material and (b) a solidified particulate mixture of (i) free fatty acid and (ii) a calcium salt of a fatty acid, the calcium salt of a fatty acid being present in a molar ratio amount in the range of from about 25% to about 55% of the amount of the free fatty acid. The preferred mixture is a solid having an onset melt point of between about 140 and 170 degrees Fahrenheit, and a hardness of from about 5 to about 15 Shore A units at 170 degrees Fahrenheit.

8 Claims, 9 Drawing Sheets

Typical Reaction Temp Profile

Related U.S. Application Data

(60) Provisional application No. 61/280,346, filed on Nov. 2, 2009.

(51) Int. Cl.
*A23K 40/10* (2016.01)
*A23K 20/24* (2016.01)
*A23K 20/20* (2016.01)
*A23K 50/10* (2016.01)

(52) U.S. Cl.
CPC .............. *A23K 50/10* (2016.05); *C07C 51/00* (2013.01); *C07C 51/41* (2013.01); *C07C 51/412* (2013.01); *C11C 1/025* (2013.01); *C11C 3/00* (2013.01)

(58) Field of Classification Search
CPC ........ A23K 20/24; A23K 20/30; A23K 50/10; A23K 40/10
USPC ....................................................... 426/601
See application file for complete search history.

(56) References Cited

U.S. PATENT DOCUMENTS

| | | | |
|---|---|---|---|
| 4,198,294 A | 4/1980 | Deane | |
| 4,221,818 A | 9/1980 | Schroeder | |
| 4,642,317 A | 2/1987 | Palmquist et al. | |
| 4,826,694 A | 5/1989 | McAskie | |
| 4,853,233 A | 8/1989 | McAskie | |
| 4,909,138 A | 3/1990 | McAskie | |
| 5,234,701 A | 8/1993 | Cummings et al. | |
| 5,382,678 A | 1/1995 | Vinci et al. | |
| 5,456,927 A | 10/1995 | Vinci et al. | |
| 5,783,714 A | 7/1998 | McKenna et al. | |
| 6,229,031 B1 | 5/2001 | Strohmaier et al. | |
| 6,576,667 B2 | 6/2003 | Strohmaier et al. | |
| 6,656,494 B1 * | 12/2003 | Nakata | A23K 40/20 424/410 |
| 6,774,252 B2 | 8/2004 | Strohmaier et al. | |
| 7,318,943 B2 | 1/2008 | Baricco et al. | |
| 2006/0045957 A1 * | 3/2006 | Bevans | A23K 40/20 426/656 |
| 2009/0220638 A1 | 9/2009 | Pablos Perez | |
| 2009/0252837 A1 * | 10/2009 | Hendel | A23K 40/10 426/74 |

OTHER PUBLICATIONS

ES2143936A1 machine translation of patent May 2000.*
Elliot et al., "Digestibility and Effects of Three Forms of Mostly Saturated Fatty Acids" Mar. 1994 *Journal of Dairy Science*, vol. 77:pp. 789-798.

* cited by examiner

PARTIAL CALCIFICATION OF FREE FATTY ACID MIXTURES, LIVESTOCK FEED COMPOSITIONS INCLUDING THEM, AND METHODS OF MAKING SAME

RELATED APPLICATION DATA

This application is a divisional patent application of U.S. patent application Ser. No. 12/755,800 filed on Apr. 7, 2010, (pending), which claims the priority benefit of U.S. Provisional Application Ser. No. 61/280,346, filed Nov. 2, 2009, each of which is incorporated herein by reference in its entirety.

TECHNICAL FIELD

The present invention relates to nutritional supplement compositions that may be used for livestock and the like, as well as to a livestock feed mixture containing them, and to their production and use.

BACKGROUND OF THE INVENTION

Methods for producing calcium soaps have been known for many years in the state of the art. Soaps are generally made from natural animal or plant fats containing triglycerides that comprise fatty acids, usually long-chain fatty acids, attached to the glycerol skeleton, which form salts by means of a process of saponification in the presence of bases.

The fatty acids that most commonly form part of these triglycerides are long-chain fatty acids such as oleic, stearic, palmitic, myristic, lauric, linoleic and linolenic acids. Fatty acids with much shorter chains also appear, such as butyric, capric, caprylic and caproic acids.

Strong inorganic alkaline metal bases, such as sodium hydroxide or potassium hydroxide, are chosen as suitable bases for the saponification reaction. In general, alkaline soaps are produced and their use is limited to cosmetics.

In the production of calcium soaps, calcium oxide (CaO) is added to the fats instead of adding alkaline metal hydroxide, which conditions the other parameters of the saponification reaction.

U.S. Pat. No. 4,642,317 discloses a process that makes it possible to increase the proportion of fat fed to ruminants, without having a deleterious effect on the rumen microorganisms, which consists of supplying the animals with fatty acids in the form of previously prepared calcium salts. One of the examples of how to produce the salts from natural fats mentions the prior saponification of the fats with sodium or potassium hydroxide, the separation of the phase containing the alkaline metal salts and the subsequent dissolution of the phase in aqueous medium and mixing it with calcium salts.

U.S. Pat. No. 4,826,694, U.S. Pat. No. 4,853,233 and U.S. Pat. No. 4,909,138 also disclose compositions for feeding ruminants wherein the main component (60-80% of the composition) is calcium or magnesium salts of longer-chain fatty acids (mainly with 14 to 18 carbon atoms), although it is also mentioned that the presence of triglycerides (5%-15%) in the end product is important for the composition to be useful as feed for ruminants. The patents also disclose an apparatus and a process for producing the intended compositions, the process comprising, in this case, mixing one or more basic oxides (preferably CaO) in excess with the fatty acids and triglycerides and with water and, optionally, with an additional nutritional material as a source of proteins, thoroughly homogenizing the mixture to bring about the exothermic reaction that forms the corresponding fatty acid salts, then spreading the mixture over a flat surface so that most of the water evaporates. It is mentioned that one of the preferred embodiments of the process involves pre-heating the fatty acids, e.g. to 80 degrees C.-100 degrees C., before mixing them with the source of basic oxide, which is preferably lime (CaO).

Modifications to this basic process have subsequently been disclosed. For example, U.S. Pat. No. 5,234,701 discloses the inclusion of an aqueous solution of sodium carbonate-bicarbonate, which is a residual effluent by-product of a bicarbonate production process, as the aqueous medium for the calcium salt-forming reaction. This addition of sodium carbonate-bicarbonate seems to increase the efficiency of the process, thanks to the formation of a reaction intermediate consisting of the fatty acid sodium salt, which facilitates the formation of the corresponding calcium salt.

Other patents stress the importance of the reaction conditions to produce products with suitable characteristics when using sources of fatty acids wherein a high proportion thereof are present in the form of triglycerides. Thus, for example, U.S. Pat. No. 5,382,678 discloses the importance of mixing the source of fatty acids with the source of alkaline earth metal prior to adding water so that the end product is not a powdery solid, but takes the form of tackless free-flowing granules. It also discloses the importance of maintaining the temperature of the reaction medium at a suitable value (40 degrees C.-130 degrees C.; 110 degrees C. is used in the examples) and for a sufficient time to hydrolyze most of the glycerides that are present, releasing fatty acids that produce the desired alkaline earth metal salts.

U.S. Pat. No. 6,229,031 also highlights the importance of maintaining a suitable temperature for long enough to achieve the saponification of fatty starting materials with more than 45% triglycerides, again mentioning the need to supply the reaction mixture with additional heat as well as that generated by the exothermic reaction itself. In this case, the suitable temperature intervals mentioned are higher (90 degree C.-250 degrees C.), with higher temperatures being preferred the lower the percentage of CaO that is added, which must be between 10% and 30% of the final composition.

U.S. Pat. No. 6,576,667 and U.S. Pat. No. 6,774,252 mention that the final triglyceride content must not exceed 5% of the total composition to prevent undesired alterations during storage, suggesting that the best way to achieve sufficient saponification when using fatty materials rich in triglycerides with a high omega-3 fatty acid content is to use 2 to 3 equivalents of CaO relative to the starting material and 2 to 5 equivalents of water relative to the CaO.

U.S. Published Patent Application No. 20090220638 discloses a process of mixing the natural fats or oils with the calcium oxide, then adding water to the mixture and applying heat in a high pressure reactor. After reacting the fats and/or oils with calcium oxide, the reaction mass is allowed to cool. The calcium soap thus produced contains glycerol from the saponification of the triglycerides. No further washing, concentration (e.g. under vacuum conditions), or similar steps are necessary. The soap need only be formed using conventional techniques of extrusion into blocks, pelletization, compression, granulation, etc. This reference discloses calcium soaps with a high fatty acid content (82-86%) are directly obtained after the saponification process, and is typical of attempts to carry out saponification more effectively, and to handle purification of the saponification reaction mixture (i.e., by using significant excess calcium oxide to drive the reaction to 100% glycerol, etc.).

Other patents relating to calcium soaps in animal feed compositions include U.S. Pat. Nos. 7,318,943; 6,229,031; 5,783,714; 4,221,818; 4,198,294; 4,062,988 and 4,016,296.

The foregoing references are hereby incorporated herein by reference.

Accordingly, the prior art has attempted to improve saponification processes applied to fats to maximize the amount of fatty acid salts obtained.

Typical of products currently on the market are 100% calcium soaps, such as Megalac, commercially available from Volac Limited of Royston, England. These products are 100% salts usually of palm oil or soybean oil fatty acids. Such products are generally made by saponification of triglyceride fats, usually palm oil or soybean oil, with technology that is well known. The 100% calcium soaps have a very high melt point (and actually decompose before melting) and thus cannot be prilled effectively.

Beyond the problems of creating calcium salts of fatty acids of sufficient nutritive value and digestibility (i.e., relatively high salt/free acid ratio, especially for ruminants), another set of concomitant problems are associated with the transportation and use of nutritional supplements of this sort relate to their transport, storage, handling and dispensing, and use in processing. One of the problems associated with free fatty acid mixtures (100% non-salted) is that they tend to have relatively low onset melting points such that they may melt when exposed to elevated ambient temperature, such as when stored in silos, packaged in bags, subjected to the heat associated with processing or milling the material with base particulate feeds, or otherwise transporting the material in warmer weather or warm climates.

The relatively low onset melting points also adversely affect handling and dispensing, as it more preferable to handle and dispense materials, both as a consumer and in industrial processing, that flow as a relatively dry, non-tacky particulate.

Another related problem is that the 100% free fatty acid products are subject to caking and agglomeration upon being subjected to pressure, whether as a result of storage in silos, packing and transport in bags, etc.

Likewise, where it is desired to blend or mill such nutritional supplements so as to produce particulate livestock feed blends, current free fatty acid products are subject to melting or liquefaction during processing, making them unsuitable for this type of industrial processing of this type. In this regard, while 100% salt products do have acceptable bulk handling properties and can be pelleted, they cannot be prilled. The 100% calcium salted fatty acid products typically are all made from palm oil or soybean oil and with the higher unsaturated fatty acid level, these products have a negative nutritional effect on the rumen relative to the more saturated free fatty acid mixtures like Energy Booster 100 (EB 100), commercially available from MSC Animal Nutrition of Adell, Wisconsin.

Accordingly, there remains a need for nutritional supplements comprising fatty acid mixtures or calcium salts of fatty acids that feature the required nutritive value and digestibility, yet are improved with respect to properties that are important to the transportation, storage, handling and industrial processing applied in the particulate livestock feed blends.

SUMMARY OF THE INVENTION

The present invention includes a nutritional supplement composition that may be used for livestock and the like, as well as to a livestock feed mixture containing same. Also included are methods of preparing the nutritional supplement composition, the livestock feed mixture, as well as methods of providing nutrition to livestock and the like.

The present invention includes a method of partially salting (calcifying/neutralizing) free fatty acids such that they can be prilled or flaked, exhibit improved compaction in bulk storage, improved flow and handling properties (flow from bulk bins, through augers, etc.), and can be processed through traditional feed pelleting mills to make a pelleted feed.

Although not limited to the theory of the invention, it is believed these improved properties are a result of increased onset melt point and hardness vs. temperature, as compared to mixture of free fatty acids.

The preparation of 100% salts of fatty acids is well known and these materials are typically prepared by well established processes of saponification of triglyceride fats and oils.

In contrast to prior art methods, it is preferred that the process of the present invention starts with free fatty acids rather than triglycerides, and produces directly a partially salted (calcified, neutralized) calcium salt of the starting fatty acid mixture, that is, the preferred starting material consists essentially of a fatty acid or fatty acid mixture. By simply neutralizing a mixture of free fatty acids with, for instance, calcium oxide (i.e., no triglycerides present, no excess calcium oxide, and no glycerol produced (which then has to be separated)), the product of the present invention avoids these disadvantages associated with products made from fats directly. The process of the present invention may also start with fats with the purification of the fatty acids prior to further partial salting.

The free fatty acid products (like EB 100) have problematic flow problems, and thus cannot be handled or used in bulk, and cannot be pelleted.

The 100% salt products do have good bulk handling properties and can be pelleted but they cannot be prilled. The 100% calcium salted fatty acid products are all made from palm oil or soybean oil and with the higher unsaturated fatty acid level, these products have a negative nutritional effect on the rumen relative to the more saturated free fatty acid mixtures like EB 100.

As a result of the process of the present invention, one may produce a partial calcium salt of fatty acid mixtures, i.e., from fatty acid mixtures such as those exemplified by EB100 fatty acid mixtures, and thereby produce products that have the best properties of both state of the art technologies, i.e., EB100 free fatty acids and Megalac 100% calcium salts of palm oil fatty acids.

The partially salted fatty acid mixture of the present invention may be prilled or flaked, in accordance with methods known and used in the art.

The preferred fatty acid made and used in the present invention is a mixture of tallow-free fatty acids and the calcium salts of tallow fatty acids, although the invention may be produced or practiced using any fatty acid mixture, although with other mixtures, one may have to use higher percent calcium for lower melting/softer mixtures. It is also preferred that the free fatty acids used in accordance with the present invention include those having a degree of unsaturation such that the iodine number is less than 20, most preferably less than 10.

Calcium may be incorporated in any form adapted to form the salt(s) of the fatty acid(s), as is known in the art, such as in the form of calcium oxide or calcium hydroxide, in an amount equivalent to about 25% to about 55% on a molar basis; i.e., in the range of from about 25 to about 55% of the total moles of the tallow fatty acid(s), such that they are converted (neutralized) to their calcium salts.

The melt point and hardness are a function of the percent calcification (i.e., percent neutralization). It is preferred that the onset melt point is about 170 F, although commercially important improved properties for handling, flow and pelleting can be obtained at melt points below 170 (though a melt point of 120-130 F such as that of commercially available EB100 is too low), and that the temperature for hardness of 15 Shore A units is about 170 F. A Shore A hardness less than 15 at 170 F (e.g. Shore A of 5-10 at 170 F) or a Shore A hardness of 15 at a lesser temp than 170 F (e.g. Shore A of 15 at say 150 F) likely will yield good commercially important improved properties, though it is known that the properties of free fatty acid mixtures like commercially available EB100 or its competitors do not have sufficient Shore A hardness at 100-120 F to demonstrate improved properties for handling, flow and pelleting.

In contrast with current products, some of the novel properties and uses of the fatty acid mixtures of the present invention include that it may be stored, transported and used in bulk (without compaction or disadvantageous liquefaction), while comparative products, such as EB 100 (and other similar mixtures of free fatty acids from tallow, palm or soy) cannot.

As one measure of the compressibility of the fatty acid mixtures of the present invention, a 50-100 gram/weight at 50 degrees centigrade for 1 hour (about 2 psi-4 psi) did not result in compaction sufficient to restrict the ability of the flaked or prilled product to be poured (which conditions brought about compaction of EB 100).

One aspect of the present invention is drawn to a feed supplement for increasing the fat intake level of animals, including animal feed and the fatty acid mixture of the present invention. The animal feed typically may be a dry feed.

The fatty acid mixtures of the present invention may be used for pelleted feed applications while comparative products, such as EB 100 and other similar mixtures of free fatty acids from tallow, palm or soy, cannot be pelleted.

The fatty acid mixtures of the present invention may stored, transported and used in dairies in hot climates (e.g., Florida, Arizona and New Mexico) while comparative products, such as EB 100 (and other similar mixtures of free fatty acids from tallow, palm or soy) cannot be handled in these climates without adverse effects on their physical form.

The fatty acid mixtures of the present invention also feature controllable, increased onset melt point and controllable, increased hardness at all temperatures relative to free fatty acid mixtures. The present invention thus offers a method by which the onset melt point can be controlled and varied.

While a 100% calcium salt of a free fatty acid mixture of oils like palm oil and soy (which are liquid at room temperature) not only produces a solid product but one that has good flow properties and can be pelleted, it is also well known that the unsaturated fatty acids present in palm and soy have a negative effect on the rumen which limits the dose that can be fed to dairy cattle.

It is also well known that mixtures of tallow fatty acids (with the lower degree of saturation compared to palm oil and soy are solids at ambient temperature), can be prilled, but do not have good flow properties and cannot be pelleted. It is also well known that tallow fatty acids, owing to their low level of unsaturation, do not have a negative impact on the rumen exhibited in the palm oil and soy fatty acid blends.

As to the increased onset melt point, a partially salted calcium salt of a fatty acid mixture is a complex mixture of lower melting fatty acids and non-melting calcium salts. Accordingly, these partially calcified calcium fatty acid mixtures would likely not exhibit an increase in onset melt point since the non-salted fatty acids would melt at their normal melt point and the calcium salts would just be suspended in the matrix of fatty acids. By virtue of the present invention, and while not limited to the theory by which it operates or achieves beneficial results, it has been discovered that, by mechanisms not fully understood, the calcium salts of a fraction of the free fatty acids present seem to complex with the remaining free fatty acids to form a mixture that has an increased onset melt point. This increase in melt point was discovered to be positive and non-linear with increasing percent calcium.

With respect to the hardness versus temperature, by the same rationale as for increased onset melt point, it was not anticipated that the partial salted calcium fatty acids would exhibit such an improved hardness relative to the free fatty acids. What was discovered was that by increasing the degree of salting by increasing the percent of calcium salts of the fatty acids present that, by mechanisms not fully understood, the calcium salts of a fraction of the free fatty acids present, seem to complex with the remaining free fatty acids to form a mixture which is harder (as measured by Shore A) at any given temperature up to the melt point relative to free fatty acid mixtures. This increase as with onset melt point is also non-linear.

The product of the present invention compares favorably to prior art formulations, such as that represented by Energy Booster 100 (EB100) commercially available from MSC Animal Nutrition of Adell, Wisconsin. The EB100 is a prilled product, but may be made and sold as a flaked product. Prilling is a spray chilling process wherein the liquid fatty acid mixture is sprayed at the top of a tall tower into a chilled air stream forming very small spheres. The EB100 is a mixture of tallow free fatty acids (from animal fat), and features an onset Melt Point ≤130 F and a temperature for Hardness of 15 Shore A units at 120 F. It may be used as an energy source for high producing dairy cows. The problems associated with this product include that it cannot be used in bulk applications (super sacks, bins, silos, trucks, etc.) due to compression into blocks, chunks, bridging, etc. In addition, it cannot be used for pelleted feed applications as pellet mash is at 160-165 degrees F. and then is heated higher through the dies, because EB100 melts at 130 degrees F. and thus binds the augers, sticks to the mash tank, and forms a soft pellet. It cannot be used conveniently on dairies in hot climates (e.g., Florida, Arizona and New Mexico) owing to its susceptibility to surface melting and resultant compaction.

In general terms, the invention thus includes a method of producing a partially calcified free fatty acid mixture, a partially calcified free fatty acid mixture, a livestock feed mixture containing a partially calcified free fatty acid mixture, a method of producing a livestock feed mixture containing a partially calcified free fatty acid mixture, a method of providing nutrition to livestock by feeding a mixture containing a partially calcified free fatty acid mixture, and a method of providing nutrition to livestock by feeding a mixture containing a partially calcified free fatty acid mixture.

The method of producing a partially calcified free fatty acid mixture comprises the steps of: (a) preparing a mixture of: (i) an amount of a free fatty acid; and (ii) an amount of a calcium-containing material comprising a calcium-containing basic compound adapted to form a calcium salt of the fatty acid, the calcium-containing material being present in a molar ratio amount in the range of from about 25% to about 55% of the amount of a free fatty acid; and (b) maintaining the mixture at sufficient temperature and for sufficient amount of time so as to form a mixture of free fatty acid and calcified free fatty acid. It will be appreciated that the mixture of free fatty acid and calcified free fatty acid may be obtained either by mixing the already salted fatty acid with free fatty acid in a melt to obtain the desired ratio, or by proceeding from and free fatty acid (or mixture thereof) and subjecting it to a partially salting reaction to obtain the desired ratio.

The free fatty acid may be selected from the group consisting of tallow and non-tallow fatty acids, and mixtures thereof, and the non-tallow fatty acids may be selected from the group consisting of fatty acids from palm oil, soy oil, fish oil, linseed oil and flax oil, and mixtures thereof.

It is preferred that the reaction mixture is maintained at a temperature in the range of from about 240 degrees to about 260 degrees Fahrenheit during step (b).

The mixture may be additionally subjected to a prilling process or a flaking process, depending upon the desired product logistics parameters (storage, transport, etc.) and application.

The partially calcified free fatty acid mixture of the present invention generally includes a composition comprising, and preferably consisting essentially of, a solid particulate mixture of free fatty acid and a calcium salt of a fatty acid, the calcium salt of a fatty acid being present in a molar ratio amount in the range of from about 25% to about 55% of the amount of the free fatty acid.

It is preferred that the free fatty acid comprises tallow fatty acid, and that the calcium salt of a fatty acid comprises a calcium salt of a tallow fatty acid, although the free fatty acid may be selected from the group consisting of tallow and non-tallow fatty acids, and mixtures thereof. The non-tallow fatty acids may be selected from the group consisting of fatty acids from palm oil, soy oil, fish oil, linseed oil and flax oil, and mixtures thereof.

It is preferred that the mixture is a solid having an onset melt point of at least 170 degrees Fahrenheit, and that it have a hardness of at least about 15 shore A units at 170 degrees Fahrenheit, although one may adjust the properties slightly with a range of a hardness of lesser Shore A than 15 at 170 F (e.g. Shore A of 5-10 at 170 F, more preferably 10-15 at 170 F) or a Shore A hardness of 15 at a lesser temp than 170 F (e.g. Shore A of 15 at 140-170, such as Shore A of 15 at 150 F) while maintaining the desired beneficial properties. Most preferably, the mixture is a solid having an onset melt point of at least 170 degrees Fahrenheit, and a hardness of up to 15 Shore A units (typically from about 5 to about 15 units) at 170 degrees Fahrenheit.

The invention also includes a livestock feed mixture containing a partially calcified free fatty acid mixture, the livestock feed composition comprises, and preferably consists essentially of: (a) a solid particulate livestock feed material and (b) a solidified particulate mixture of (i) free fatty acid and (ii) a calcium salt of a fatty acid (as described herein), the calcium salt of a fatty acid being present in a molar ratio amount in the range of from about 25% to about 55% of the amount of the free fatty acid.

The invention also includes a method of producing a livestock feed composition containing partially calcified free fatty acid mixture, comprising the steps of: (a) preparing a blend of: (i) a solid particulate livestock feed material and (ii) a solid particulate mixture of free fatty acid and a calcium salt of a fatty acid (as described herein), the calcium salt of a fatty acid being present in a molar ratio amount in the range of from about 25% to about 55% of the amount of the free fatty acid, so as to obtain a solid particulate livestock feed composition; and (b) rendering the blend into a solid particulate livestock feed composition.

The partially calcified free fatty acid mixture may be produced by a prilling process or a flaking process.

The solid particulate livestock feed composition preferably is rendered into pellets, although other physical forms may be used.

The present invention further includes a method of providing nutrition to livestock by feeding a mixture containing a partially calcified free fatty acid mixture, the method comprising administering to a livestock animal a solid particulate livestock feed composition comprising: (a) a solid particulate livestock feed material; and (b) a solid particulate mixture of free fatty acid and a calcium salt of a fatty acid (as described herein), the calcium salt of a fatty acid being present in a molar ratio amount in the range of from about 25% to about 55% of the amount of the free fatty acid.

The solid particulate livestock feed composition preferably is in pellet form, and typically will be administered in nutritionally effective amounts in accordance with livestock care and nutrition practices known in the art.

DETAILED DESCRIPTION OF THE PREFERRED EMBODIMENTS

Figure 1:
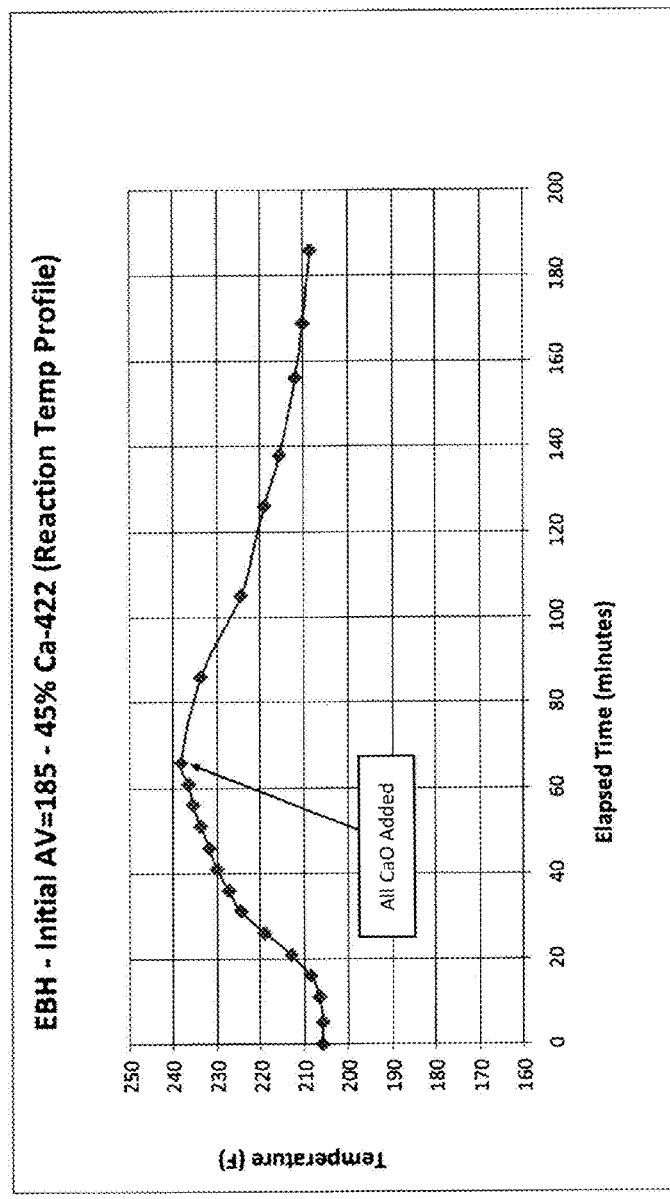
FIG. 1 is a graph of temperature versus reaction time showing a typical reaction profile as may arise in accordance with one embodiment of the present invention.
Figure 2:
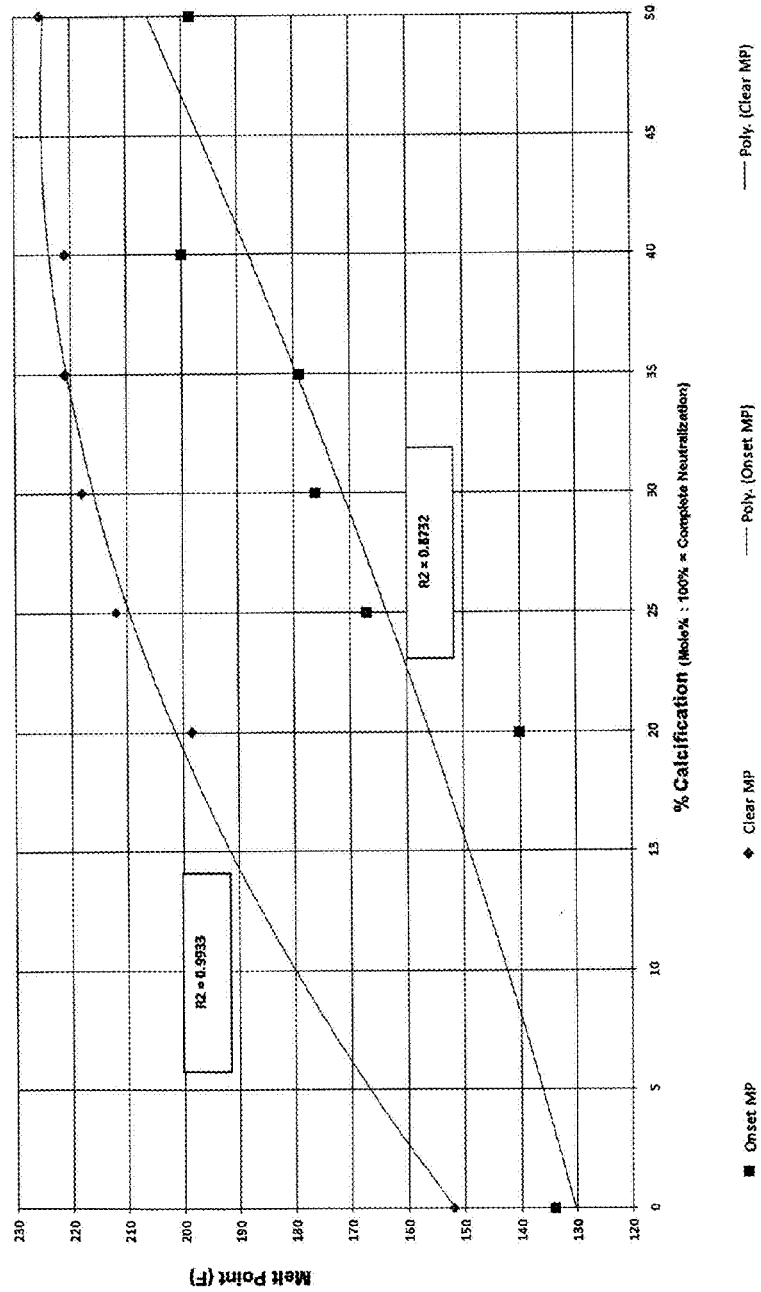
FIG. 2 is a graph of melt point versus percent calcification showing a profile as may arise in accordance with one embodiment of the present invention.
Figure 3:
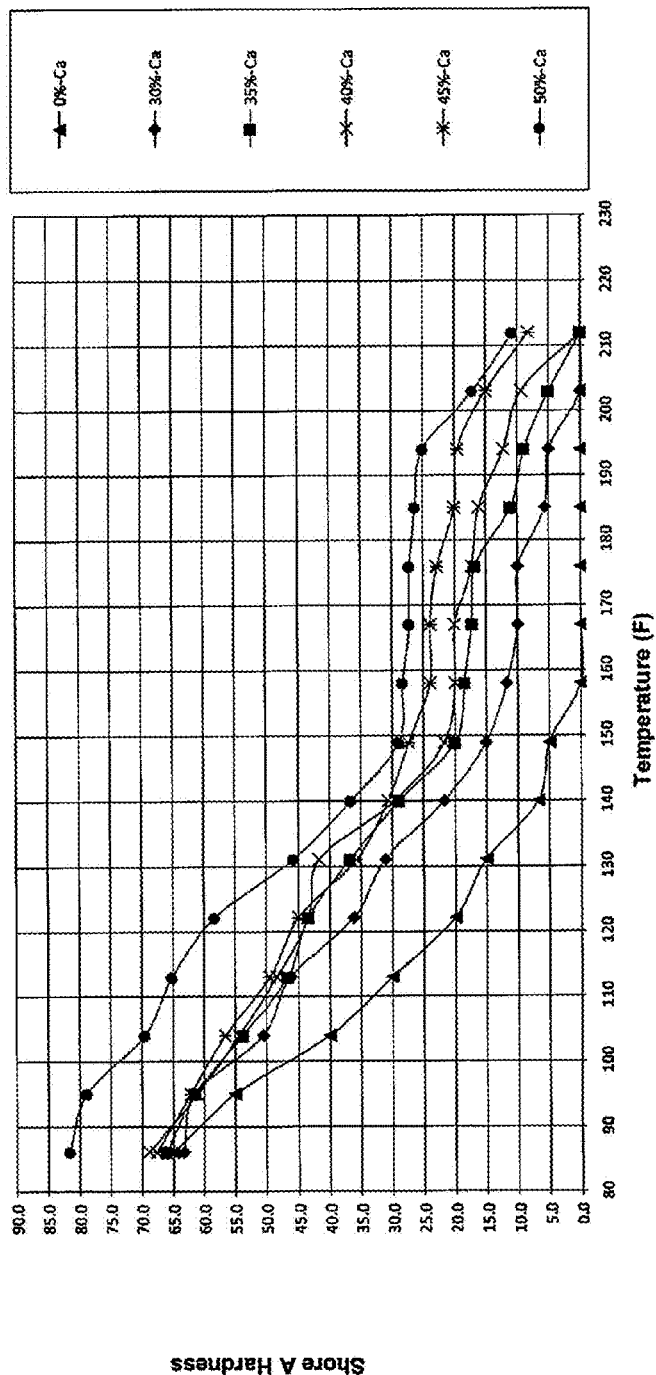
FIG. 3 is a graph of Shore A hardness versus temperature for multiple percentages of calcification, and showing a profile as may arise in accordance with one embodiment of the present invention.
Figure 4:
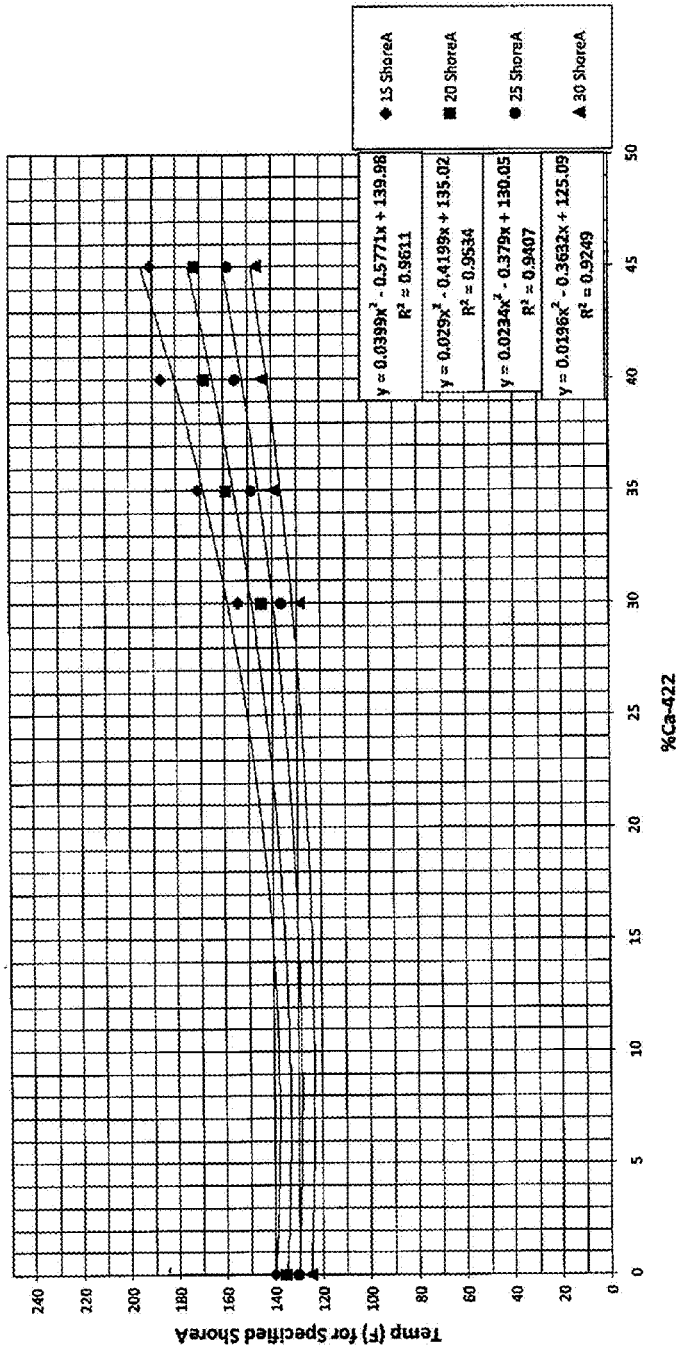
FIG. 4 is a graph of temperature for a specified Shore A hardness versus percent calcification for multiple percentages of calcification, and showing a profile as may arise in accordance with one embodiment of the present invention.
Figure 5:
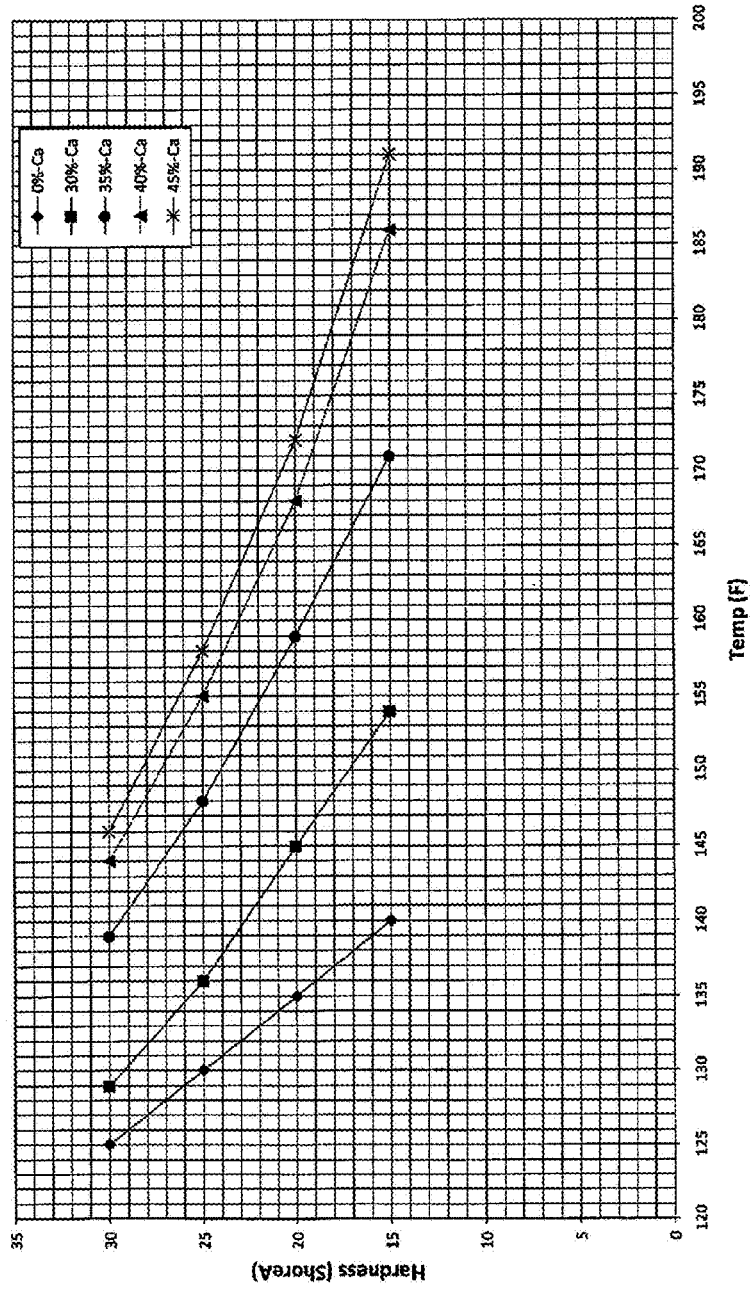
FIG. 5 is a graph of Shore A hardness versus temperature for multiple percentages of calcification, and showing a profile as may arise in accordance with one embodiment of the present invention.
Figure 6:
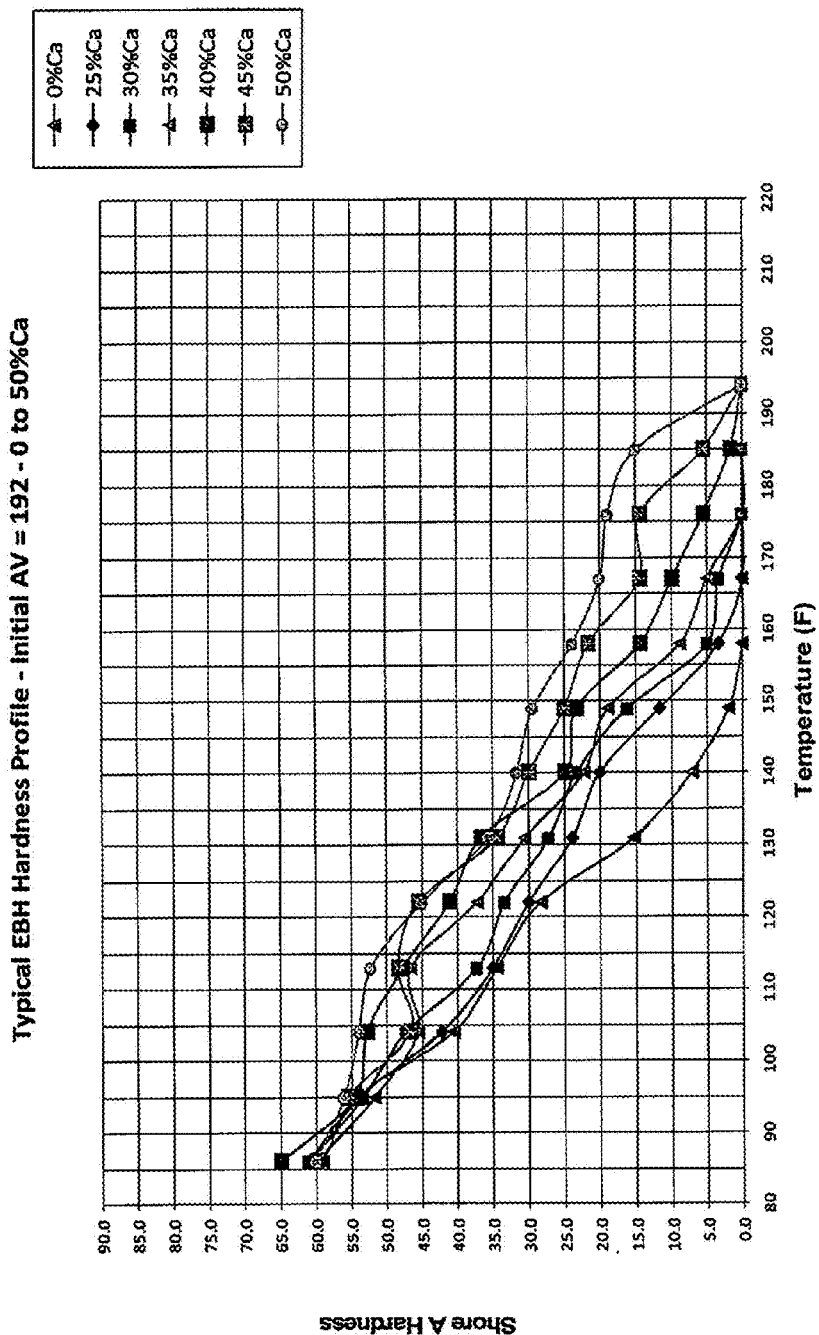
FIG. 6 is a graph of Shore A hardness versus temperature for multiple percentages of calcification, and showing a profile as may arise in accordance with one embodiment of the present invention.
Figure 7:
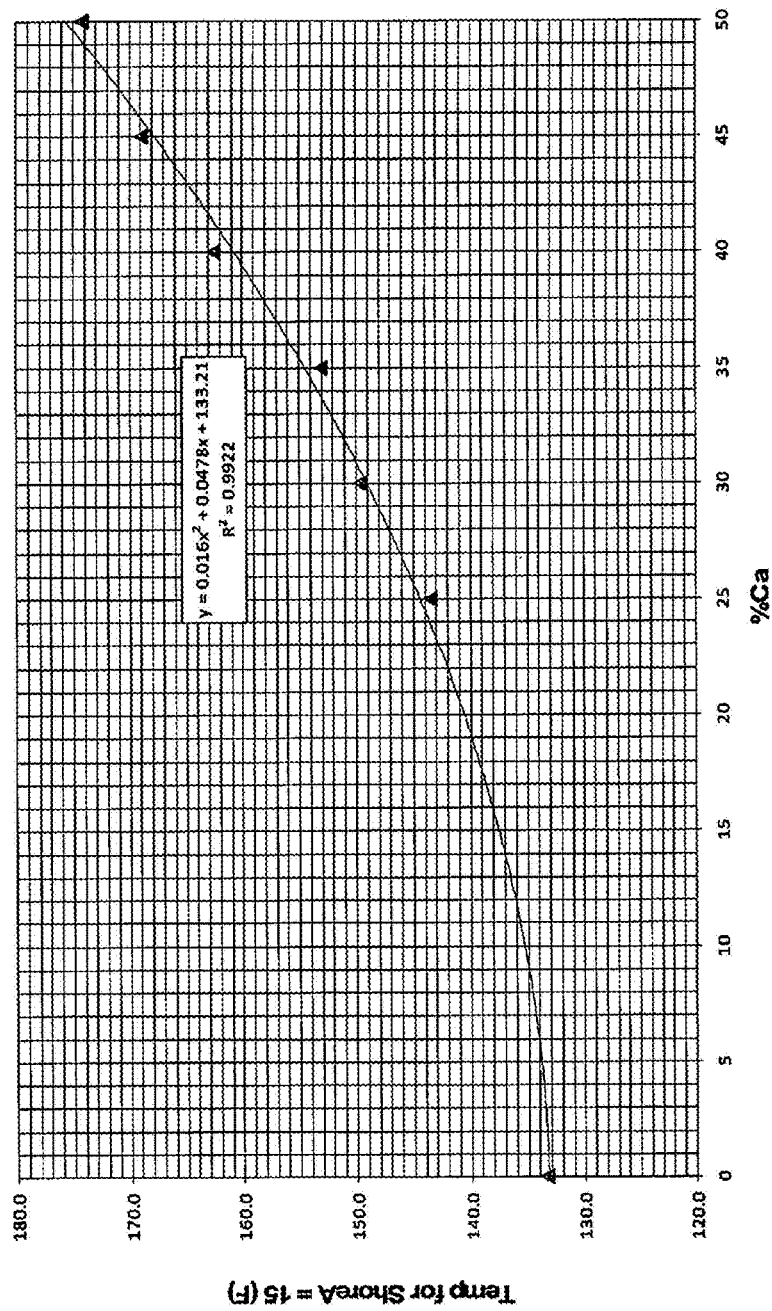
FIG. 7 is a graph of temperature for a specified Shore A hardness of 15 versus percent calcification, and showing a profile as may arise in accordance with one embodiment of the present invention.

In accordance with the foregoing summary of the invention, the following presents a detailed description of the preferred embodiments, which are considered to be the best mode thereof.

The preferred method and compositions described herein are not intended to be exhaustive or to limit the invention to the precise forms disclosed. They are chosen and described to explain the principles of the invention and the application of the method to practical uses so that others skilled in the art may practice the invention.

Example 1 of the Manufacturing Process of the Present Invention

As a preferred but non-limiting example of the method by which compositions of the present invention may be made, the following steps may be followed:

1. Heat mixture of free fatty acids to 205-240 degrees F.
2. Add desired molar equivalents of calcium as calcium oxide or calcium hydroxide with good mixing. The exothermic reaction of calcium oxide or hydroxide with free fatty acids causes temperature to rise to about 260-280 degrees F. (dependent on insulation and heat loss of reactor system).
3. Hold reaction mixture at 240-260 degrees F. until reaction is complete as measured by change in Acid Value (AV). The reaction may be monitored by determining Acid Value (AV) of the material; for example: for a target of 40% calcification the AV at completion would be about 60% of the starting AV (i.e., AV final=0.6*AV starting).
4. When reaction is complete as determined in 3 above, material is either prilled in a prilling (spray chilling) tower or flaked on a rotary drum flaker by use of methods and apparatus well known in the field.

Normally, the maximum percentage of fat attainable for the 100% calcium soaps or the prior art is about 80-82% due to the 100% calcium level while the maximum percentage of fat attainable is over 90 percent fat for products made in accordance with the present invention.

While the 100% calcium soap products do not melt, the melt point and hardness can be controlled for the partially calcified products made in accordance with the present invention.

The calcium soaps have historically been made from palm oil and soybean oil. Both these oils and free fatty acid mixtures from these oils are liquids at room temperature and so to sell these products as a solid into the dairy industry the companies using these starting materials had to make the calcium soaps.

Example 2 of the Manufacturing Process of the Present Invention

A repeatable, controlled process was developed for partial calcification of free fatty acids which included heating melted free fatty acids to 205 F, slowly adding the calculated amount of calcium oxide and allowing the reaction to proceed for approximately 2 hours after all calcium oxide was added. The temperature typically rises to 230-240 F shortly after the final addition of calcium oxide and remains in the range of 220-230 F throughout the 2 hour reaction.

As an alternative to a timed reaction, the initial Acid Value (AV) can be obtained by known titration methods and the AV monitored throughout the reaction until AV value levels out (e.g. initial AV=185; for 40% calcification final AV=111).

A typical temperature-time profile is plotted in FIG. 1.

Melt Point and Hardness Properties of the Compositions

Melt point and hardness vs. temperature properties were determined for two different mixtures of fatty acids.
First Mixture=Initial AV of 185.
Second Mixture=Initial AV of 192.
Two Melt Points were determined.
Onset Melt Point=temperature at which first signs of melting are observed.
Clear Melt Point=temperature at which no solid remains.

The Hardness was determined at various temperatures with a Rex Vest Pocket 1500 Durometer with a Shore A hardness scale.

Results are shown in FIGS. 2-7, the composition(s) made in accordance with the present invention are designated as "EBH."

Product Compression Properties

The product made from a fatty acid mixture with initial AV=185 was calcified to 35% Ca and subjected to a simple compression test along with prilled 0% starting material and a 100% Ca-Salt commercial product (i.e., Megalac).

Figure 8:
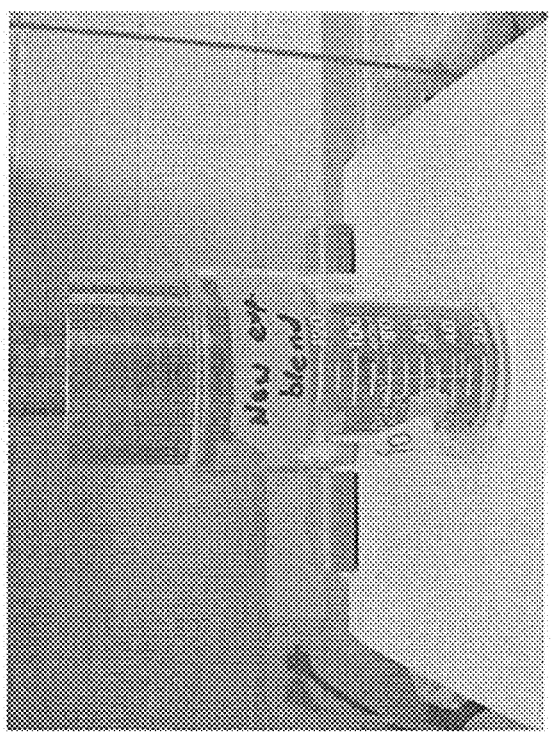
FIG. 8 is a picture of a compression testing experimental setup used to assess the physical characteristics of compositions of the present invention.

The set-up used to do this test is shown in FIG. 8.

Prilled materials were placed into a beaker with weights compressing the prills to create either 2 psi or 4 psi to simulate the compressive forces of bulk storage.

The weighted beaker of prills was placed in a 50 degrees C. oven for 30 min and then cooled to room temperature and tested for pourability and appearance.

Figure 9:
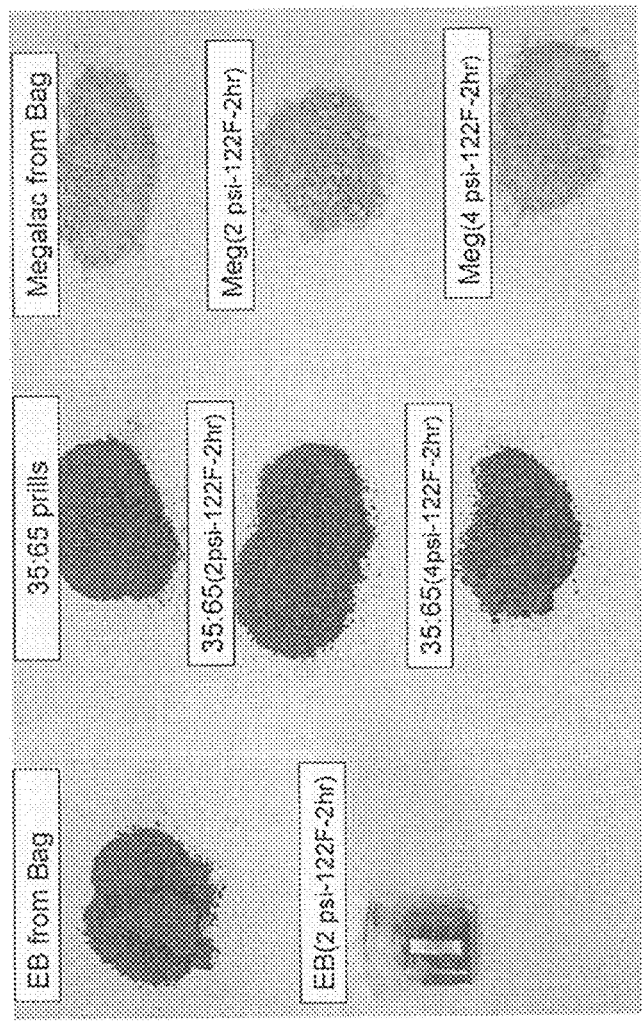
FIG. 9 is a picture of test results of particulate matter as a result of compression testing, showing the comparative physical characteristics of compositions of the present invention and those of the prior art.

Pictures were taken and are shown in FIG. 9.

From the data, a conclusion is that prilled 0% Ca starting material melted-compressed such that it was not pourable, while the 35% Ca prilled material showed no significant signs of compression and poured out of the beaker very well.

Product in accordance with the present invention may be suitable for bulk storage, such as in silos or otherwise. It may also be bagged for storage and can even be transported or stored in relatively warmer climates. By contrast prior art formulations, such as the EB100 product and other mixtures of free fatty acids from tallow, palm or soy cannot.

The product of the present invention also features a controllable, increased onset melt point, as well as a controllable, increased hardness at all temperatures relative to free fatty acid mixtures of the prior art.

The product can be used as a feed supplement and may be formulated into fat supplementing animal feeds for livestock and the like. Examples may include dairy cow rations. The animal feeds may be rendered into particulate or pelletized form in accordance with and through the use of equipment and methods known and used in the art. By contrast, the pelleted feed applications compare favorably to the EB100 product and other mixtures of free fatty acids from tallow, palm or soy, which cannot be effectively pelleted.

While specific configurations and arrangements are discussed, it should be understood that this is done for illustrative purposes only. A person skilled in the relevant art will recognize that other process and composition variations can be used without departing from the spirit and scope of the invention. It will be apparent to a person skilled in the relevant art that this invention can also be employed in a variety of other applications.

What is claimed is:

1. A composition comprising a solidified particulate mixture of:
    free fatty acid; and
    neutralized fatty acid comprising a calcium salt of the fatty acid in an amount from about 25% to about 55%, on a molar basis, of total fatty acid in the mixture;
    wherein the composition has an onset melt point of from 170° F. to 205° F.

2. A composition according to claim 1 comprises tallow, non-tallow fatty acids, or a mixture thereof.

3. A composition according to claim 1 comprises a non-tallow fatty acid comprising a fatty acid from palm oil or flax oil.

4. A composition according to claim 1 wherein the composition has a hardness of at least about 15 shore A units at 170° F.

5. A livestock feed composition comprising:
a solid particulate livestock feed material; and
a solid particulate mixture having an onset melt point of from 170° F. to 205° F. and comprising:
free fatty acid; and
neutralized fatty acid comprising a calcium salt of the fatty acid in an amount from about 25% to about 55%, on a molar basis, of total free fatty acid in the solid particulate mixture.

6. A livestock feed composition according to claim 5 wherein the free fatty acid comprises tallow, non-tallow fatty acids, or a mixture thereof.

7. A livestock feed composition according to claim 5 wherein the free fatty acid comprises a non-tallow fatty acid comprising a fatty acid from palm oil, soy oil, fish oil, linseed oil or flax oil.

8. A livestock feed composition according to claim 5 wherein the mixture has a hardness of from about 5 to about 15 Shore A units at 170° F.

\* \* \* \* \*

UNITED STATES PATENT AND TRADEMARK OFFICE
CERTIFICATE OF CORRECTION

PATENT NO. : 9,867,388 B2  
APPLICATION NO. : 14/814936  
DATED : January 16, 2018  
INVENTOR(S) : Trevor Tomkins Page 1 of 1

It is certified that error appears in the above-identified patent and that said Letters Patent is hereby corrected as shown below:

In the Claims

Column 10, Line 63, Claim 2 "claim 1 comprises" should read --claim 1 wherein the free fatty acid comprises--

Column 10, Line 65, Claim 3 "claim 1 comprises" should read --claim 1 wherein the free fatty acid comprises--

Column 10, Lines 66-67, Claim 3 "palm oil or flax oil" should read --palm oil, soy oil, fish oil, linseed oil or flax oil.--

Signed and Sealed this  
Fifth Day of November, 2019

Andrei Iancu  
*Director of the United States Patent and Trademark Office*